(12) United States Patent
Lentner et al.

(10) Patent No.: US 12,213,704 B1
(45) Date of Patent: Feb. 4, 2025

(54) MODULAR SPINAL FIXATION SCREW

(71) Applicant: Complex Spinal, LLC, Palm Beach Gardens, FL (US)

(72) Inventors: Greg Lentner, Palm Beach Gardens, FL (US); John E. Hammill, Sr., Palm Beach Gardens, FL (US)

(73) Assignee: Complex Spinal, LLC, Palm Beach Gardens, FL (US)

( * ) Notice: Subject to any disclaimer, the term of this patent is extended or adjusted under 35 U.S.C. 154(b) by 0 days.

(21) Appl. No.: 18/746,748

(22) Filed: Jun. 18, 2024

(51) Int. Cl.
*A61B 17/70* (2006.01)
*A61B 17/86* (2006.01)

(52) U.S. Cl.
CPC ...... *A61B 17/7034* (2013.01); *A61B 17/8635* (2013.01); *A61B 17/8685* (2013.01)

(58) Field of Classification Search
CPC ............ A61B 17/7034; A61B 17/8635; A61B 17/8685
USPC .................................................. 606/250–279
See application file for complete search history.

(56) References Cited

U.S. PATENT DOCUMENTS

| | | |
|---|---|---|
| 255,428 A | 3/1882 | Graham |
| 590,204 A | 9/1897 | Archer |
| 4,378,187 A | 3/1983 | Fullerton |
| 4,419,026 A | 12/1983 | Leto |
| 4,836,196 A | 6/1989 | Park et al. |
| 4,854,304 A | 8/1989 | Zielke |
| 4,887,595 A | 12/1989 | Heinig et al. |
| 4,887,596 A | 12/1989 | Sherman |
| 4,946,458 A | 8/1990 | Harms et al. |
| 4,950,269 A | 8/1990 | Gaines, Jr. |
| 5,002,542 A | 3/1991 | Frigg |
| 5,110,244 A | 5/1992 | Garman |
| 5,129,900 A | 7/1992 | Asher et al. |

(Continued)

FOREIGN PATENT DOCUMENTS

| | | |
|---|---|---|
| EP | 0836835 A2 | 4/1998 |
| EP | 0836835 A3 | 4/1998 |

(Continued)

OTHER PUBLICATIONS

Anonymous, "Versalok Low Back Fixation System—Instrumentation Manual", Wright Medical Technology, Inc.—Arlington, TN, pp. 1-10, (1997).

(Continued)

*Primary Examiner* — Eduardo C Robert
*Assistant Examiner* — Tara Rose E Carter
(74) *Attorney, Agent, or Firm* — McHale & Slavin, P.A.

(57) ABSTRACT

A modular spinal fixation screw capable of rapid linear engagement of a bone screw and a rod member. The fixation screw is coupled to a connector formed from a clamp and a collet. The collet incorporates the use of a T-shaped living hinge which facilitates both attachment of the connector to a bone screw and lessens the resistance of the collet for locking to the bone screw and rod member. The collet further includes scallops that facilitates the insertion of the spherical end of the bone screw into the collet. The clamp can be moved from a first unlocked position used for installation to a locked position securing the rod member to a pedicle bone. The clamp compresses the collet which holds the hold rod member to the bone screws in a pre-selected position by linear movement of the clamp.

9 Claims, 6 Drawing Sheets

(56) References Cited

U.S. PATENT DOCUMENTS

| | | |
|---|---|---|
| 5,133,717 A | 7/1992 | Chopin |
| 5,324,150 A | 6/1994 | Fullerton |
| 5,427,488 A | 6/1995 | Fullerton et al. |
| 5,443,467 A | 8/1995 | Biedermann et al. |
| 5,487,744 A | 1/1996 | Howland |
| 5,549,608 A | 8/1996 | Errico et al. |
| 5,569,247 A | 10/1996 | Morrison |
| 5,584,834 A | 12/1996 | Errico et al. |
| 5,591,166 A | 1/1997 | Bernhardt et al. |
| 5,613,816 A | 3/1997 | Cabahug |
| 5,628,740 A | 5/1997 | Mullane |
| 5,669,911 A | 9/1997 | Errico et al. |
| 5,683,392 A | 11/1997 | Richelsoph et al. |
| 5,716,357 A | 2/1998 | Rogozinski |
| 5,733,285 A | 3/1998 | Errico et al. |
| 5,749,690 A | 5/1998 | Kutz |
| 5,788,443 A | 8/1998 | Cabahug |
| 5,800,435 A | 9/1998 | Errico et al. |
| 5,863,293 A | 1/1999 | Richelsoph |
| 5,947,966 A | 9/1999 | Drewry et al. |
| 5,964,760 A | 10/1999 | Richelsoph |
| 5,997,539 A | 12/1999 | Errico et al. |
| 6,010,503 A | 1/2000 | Richelsoph |
| 6,050,997 A | 4/2000 | Mullane |
| 6,063,090 A | 5/2000 | Schlapfer |
| 6,090,111 A | 7/2000 | Nichols |
| 6,102,952 A | 8/2000 | Koshino |
| 6,113,600 A | 9/2000 | Drummond et al. |
| 6,132,432 A | 10/2000 | Richelsoph |
| 6,162,234 A | 12/2000 | Freedland et al. |
| 6,187,005 B1 | 2/2001 | Brace et al. |
| RE37,227 E | 6/2001 | Brodbeck |
| 6,254,602 B1 | 7/2001 | Justis |
| 6,273,888 B1 | 8/2001 | Justis |
| 6,355,040 B1 | 3/2002 | Richelsoph et al. |
| RE37,665 E | 4/2002 | Ralph et al. |
| 6,413,258 B1 | 7/2002 | Bernhardt, Jr. |
| 6,416,515 B1 | 7/2002 | Wagner |
| 6,454,773 B1 | 9/2002 | Sherman et al. |
| 6,478,798 B1 | 11/2002 | Howland |
| 6,565,565 B1 | 5/2003 | Yuan et al. |
| 6,595,992 B1 | 7/2003 | Wagner et al. |
| 6,602,255 B1 | 8/2003 | Campbell et al. |
| 6,610,062 B2 | 8/2003 | Bailey et al. |
| 6,610,063 B2 | 8/2003 | Kumar et al. |
| 6,623,485 B2 | 9/2003 | Doubler et al. |
| 6,626,906 B1 | 9/2003 | Young |
| 7,105,029 B2 | 9/2006 | Doubler et al. |
| 7,335,201 B2 | 2/2008 | Doubler et al. |
| 7,658,582 B2 | 2/2010 | Doubler et al. |
| 7,744,633 B2 | 6/2010 | Berrevoets et al. |
| RE42,867 E | 10/2011 | Hammill, Sr. et al. |
| 9,649,135 B2 | 5/2017 | Doubler et al. |
| 10,136,925 B2 | 11/2018 | Shoshtaev |
| 10,751,090 B2 | 8/2020 | Biedermann et al. |
| 2002/0114680 A1 | 8/2002 | Stoewer et al. |
| 2003/0149487 A1 | 8/2003 | Doubler et al. |
| 2005/0053423 A1 | 3/2005 | Doubler et al. |
| 2005/0096653 A1* | 5/2005 | Doubler .............. A61B 17/7037 606/277 |
| 2007/0286703 A1 | 12/2007 | Doubler et al. |
| 2010/0262196 A1* | 10/2010 | Barrus ............... A61B 17/7037 606/308 |

FOREIGN PATENT DOCUMENTS

| | | |
|---|---|---|
| EP | 0947174 A3 | 10/1999 |
| EP | 0947174 B1 | 10/1999 |

OTHER PUBLICATIONS

Anonymous, ", Strong, Simple and Low Profile—Ovation Polyaxial System", Osteotech, Inc. Spinal Systems.—Eatontown, NJ, pp. 1-6, (1999).

* cited by examiner

MODULAR SPINAL FIXATION SCREW

FIELD OF THE INVENTION

This invention relates to the field of orthopedic surgery and, in particular, to an improved modular low profile spinal fixation screw.

BACKGROUND OF THE INVENTION

Numerous devices are known for treating chronic back problems caused by intervertebral disc disease, disc deterioration, injury, and general loss of stability of the intervertebral joints. Degenerative discs can be caused from numerous diseases such as scoliosis, spondylolithesis, spinal stenosis, and so forth. Stabilization and/or arthrodesis of the intervertebral joint can reduce the pain associated with movement of a diseased or deteriorated intervertebral joint.

In order to allow for development a solid of intervertebral fusion, the spine has to be stabilized. There are many instances in which it is necessary to stabilize and fix bones and bone fragments in a particular spatial relationship to correct the location of skeletal components due to injury or disease. A now common system employs a number of bone screws placed across a discontinuity in adjacent vertebrae and connected by a rod to maintain a predetermined spatial location. The bone screws are connected together by a rod having sufficient stiffness to maintain the desired skeletal orientation. The connection between the rod and the bone screws must be strong enough to be immobile.

Conventionally a set screw would lock a rod to a connector and the bone screw. In this embodiment a bone screw is secured to the bone and connector is attached to the end of the exposed end of the bone screw. The connector is secured to the bone screw, before or after bone screw installation, and a rod attached to adjoining connectors. The connectors typically having a set screw for secured the rod to the connector, the set screw requiring a torque to lock the rod to the connector and the connector to the bone screw.

Alternatively the rod can be secured to the connector by linear engagement which eliminates torque fastening. Inventor's previous patents include U.S. Pat. Nos. 9,649,135 and 9,649,142 directed to a low profile spinal stabilization system capable of locking a spinal connecting rod to an anchored bone screw by linear engagement so as to eliminate the need apply torque for final fastening.

Improvements to the low profile spinal stabilization system to enhance coupling of a connector to a bone screw.

SUMMARY OF THE INSTANT INVENTION

The present invention is an improved modular low profile spinal fixation screw capable of rapid linear engagement of a bone screw and a rod. The fixation screw is coupled to a connector formed from a clamp and a collet. The collet incorporates the use of a living hinge which facilitates both attachment of the connector to a bone screw and lessens the resistance of the collet for locking to the bone screw and rod member. The collet further includes scallops that facilitates the insertion of the spherical end of the bone screw into the collet. The clamp can be moved from a first unlocked position used for installation to a locked position securing the rod member to a pedicle bone. The clamp compresses the collet which holds the hold rod member to the bone screws in a pre-selected position by linear movement of the clamp.

It is an objective of the present invention to provide an improved low profile spinal stabilization system capable of precise and reproducible linear engagement and disengagement.

Still another objective of the present invention is to provide a connector that provides a bottom loading low profile spinal stabilization system, the connector being attached to a bone screw after the bone screw has been anchored.

Another objective of the invention is to teach an improved collet that incorporates the use of a living hinge to facilitate attachment of the connector to a bone screw and lessen the resistance of the collet for locking. The collet further includes strategically positioned scallops that facilitate the insertion of the spherical end of the bone screw into the collet.

Yet another objective of the present invention is to provide a low profile spinal stabilization system capable of locking a spinal connecting rod to an anchored bone screw by linear engagement so as to eliminate torque fastening.

Yet a further objective of the present invention is to teach the use of a linear fastener that is adjoined to an anchored bone screw for support of ancillary devices adapted to be secured together without rotational torque forces.

Other objectives and advantages of this invention will become apparent from the following description taken in conjunction with the accompanying drawings which set forth, by way of illustration and example, certain embodiments of this invention. The drawings constitute a part of this specification and include exemplary embodiments of the present invention and illustrate various objects and features thereof.

DETAILED DESCRIPTION OF THE PREFERRED EMBODIMENTS

Figure 1A:
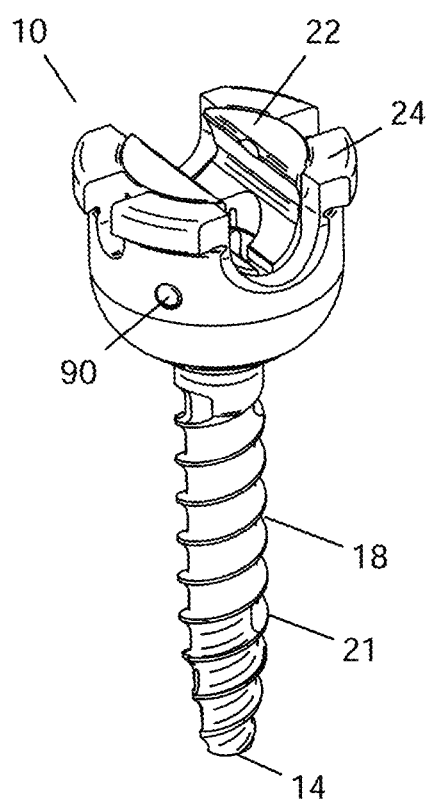
FIG. 1A illustrates a front perspective view of the modular spinal fixation screw.
Figure 1B:
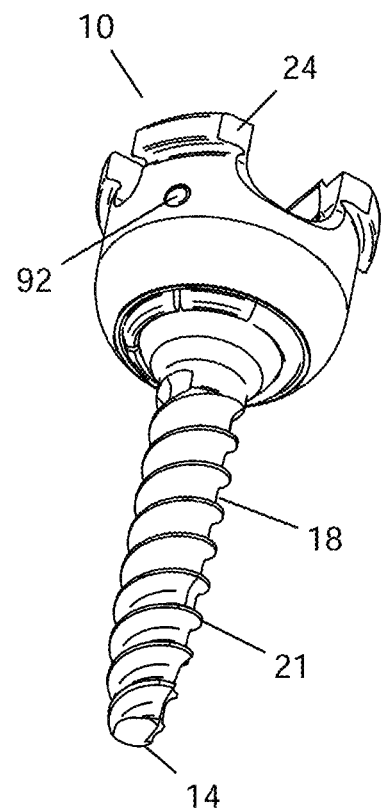
FIG. 1B illustrates a rear perspective view of FIG. 1A.
Figure 2A:
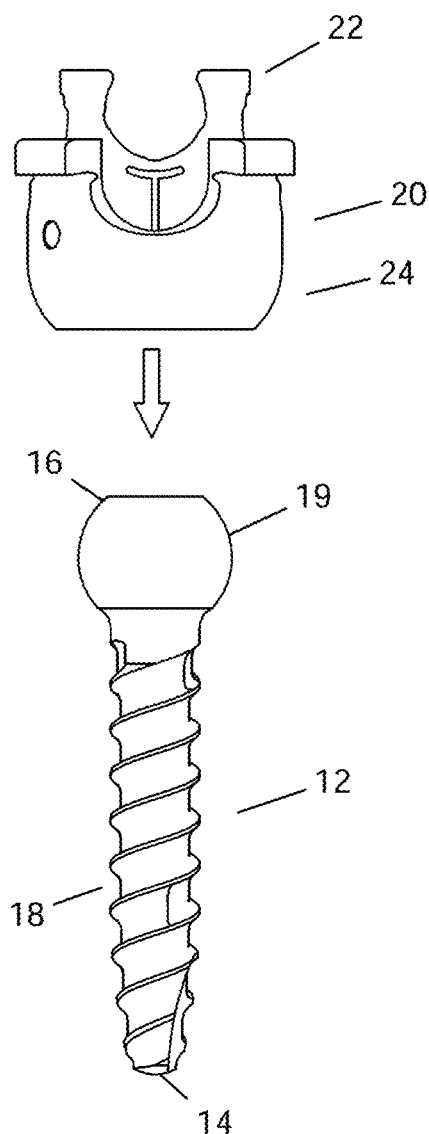
FIG. 2A illustrates a side view of the modular spinal fixation screw showing a connector during assembly.
Figure 2B:
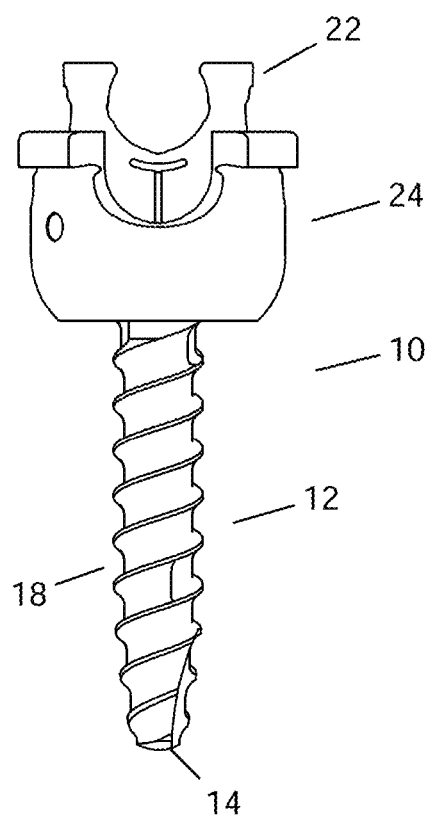
FIG. 2B illustrates a side view of FIG. 2A with the connector assembled.
Figure 3A:
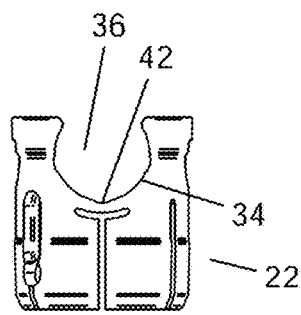
FIG. 3A illustrates a side view of a collet.
Figure 3B:
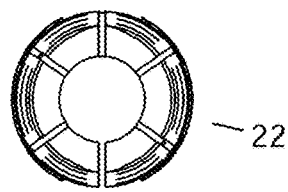
FIG. 3B illustrates a top view of FIG. 3A.
Figure 3C:
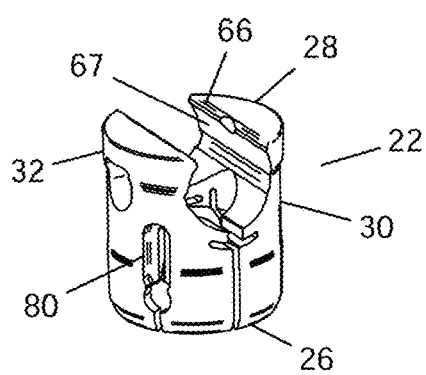
FIG. 3C illustrates an upper perspective view of FIG. 3A.

Detailed embodiments are disclosed herein; however, it is understood that the following description is provided as being exemplary of the invention, which may be embodied in various forms without departing from the scope of the claimed invention. Thus, the specific structural and functional details provided in the description are non-limiting, but serve merely as a basis for the invention defined by the claims provided herewith.

Generally speaking, various embodiments of the present invention provide for a modular spinal fixation for orthopedic rod implantation. The invention is not limited to a specific size, diameter, or length and may accommodate a patient of any size, weight, and spinal condition. By way of example, the modular spinal fixation screw employs a pedicle screw that can vary in size, diameter, or length to accommodate the patient's needs. An advantage of the instant invention includes having a low profile spinal stabilization design capable of precise and reproducible linear engagement and disengagement.

Referring now to the Figures, illustrated is a preferred embodiment of the modular spinal fixation screw 10. The modular spinal fixation screw 10 includes a bone screw 12, also referred to as a pedicle screw, having a first end 14 and a second end 16 with a threaded shank 18 therebetween. The first end 14 of the bone screw 12 provides a penetrating tip used for entering and securing to pedicle bone structure. The second end 16 of the bone screw 12 forms a spherical head portion 19. The modular spinal fixation screw 10 includes at least one continuous thread 21 on the threaded shank 18 protruding outwardly to engage with bone structure and provide stabilization of the joint. In a preferred embodiment, the modular spinal fixation screw 10 includes at least one helical thread 21 for penetration and engagement of the bone. The size, shape, and pitch of the continuous thread 21 are not limiting. The pitch of the threads 21 may be consistent or variable.

The modular spinal fixation a screw 10 includes connector 20 having a collet 22 operatively associated with a clamp 24. Pins 90, 92 coupled the collet 22 to the clamp 24. The collet 22 has a lower end 26 spaced apart from an upper end 28 with a cylindrical shaped side wall 30 therebetween. The upper end 26 forms a header 32 which protrudes outwardly from the side wall 30 with a tapered section 32 extending from the side wall 30 to the upper end 28. A u-shaped receptacle 36 extends beneath the upper end 28 and is constructed and arranged to receive a rod member 100.

Figure 5:
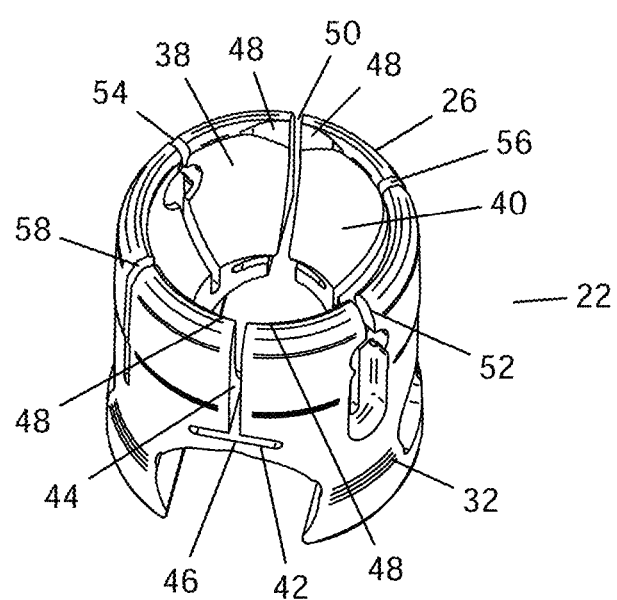
FIG. 5 illustrates a bottom perspective view of the collet lower end.
Figure 7A:
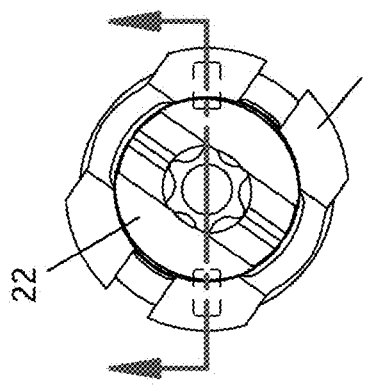
FIG. 7A illustrates a top view of the modular spinal fixation screw with an unlocked connector being placed over the bone screw.
Figure 8A:
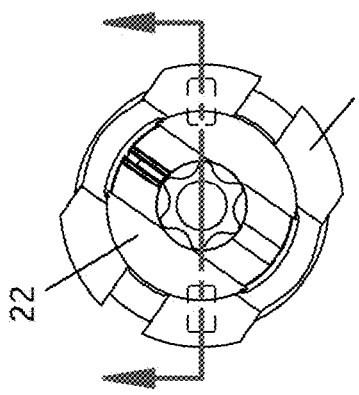
FIG. 8A illustrates a top view of the modular spinal fixation screw with an unlocked connector placed over the bone screw.

Now referring to FIG. 5, the collet lower end 26 has an inner side wall 38 forming a receptacle surface 40 sized for coupling to the head portion 19 of the bone screw 12. The receptacle surface 40 has at least one T-shaped living hinge 42 formed therein from a first relief cut 44 extending from the collet lower end 26 to a perpendicular positioned relief cut 46 juxtapositioned to the lower receptacle surface 40. Moreover, a split line 50 extends between the receptacle surface 40 and the lower end 26. The collet 22 also includes relief cuts placed between the living hinge 42 and the split line 50. In a preferred embodiment, the collet 22 includes a first pair of relief cuts 52, 54 placed between the living hinge 42 and the split line 50 and a second pair of relief cuts 56, 58 placed between the split line 50 and the living hinge 42.

The collet 22 provides proper seating of the head portion 19 along the receptacle surface 40. The living hinge 42 and the relief cuts act in such a way whereby the collet 22 is able to slightly expand and contract to adapt to the shape and size of the head portion 19. The design allows for the relief cuts to be strategically placed to facilitate attachment of the connector 20 to a bone screw 12 and ultimately lessen the resistance of the collet 22 for locking. In a preferred embodiment, the modular spinal fixation screw 10 includes side wall reliefs 48 to facilitate ease of inserting the collet 22 to the bone screw head portion 19.

During assembly, pins 90, 92 keep the connector 20 and the collet 22 together. The collet 22 includes a first and a second vertically disposed pin slot 80, 82 extending along a length of the side wall 30. Pins 90, 92 are typically welded in the body, not shown. The pins limit the movement of the collet between an open position and a locked position.

Figure 4A:
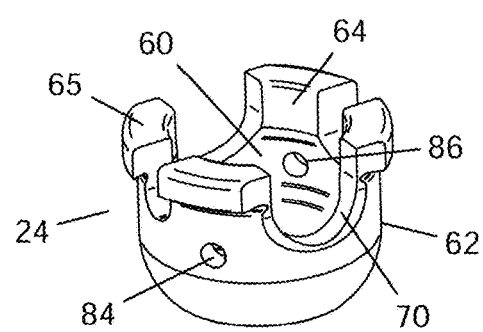
FIG. 4A illustrates an upper perspective view of the clamp.
Figure 3D:
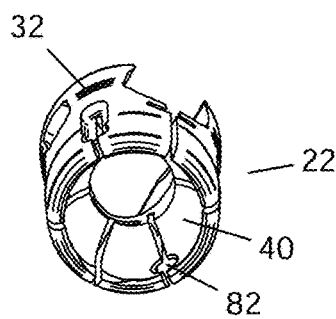
FIG. 3D illustrates a lower perspective view of FIG. 3A.
Figure 4B:
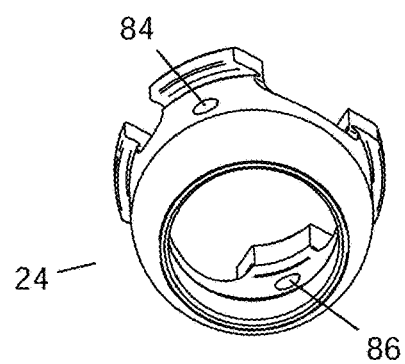
FIG. 4B illustrates a lower perspective view of FIG. 4A.

Now referring to FIGS. 4A and 4B, the clamp 24 has an elongated body with an interior wall 60 and an exterior wall 62. The interior wall includes at least one annular bulge 64 constructed and arranged to change the diameter of the collet 22 sidewall 30 when the clamp 24 is drawn over the collet 22. Similar to the u-shaped receptacle 36 on the collet 22, a rod slot 70 is constructed to accept a rod member 100. In order to receive a rod member 100, the rod slot 70 and the u-shaped receptacle 36 must be in line.

Likewise, the clamp 24 includes a first and a second pin hole 84, 86 extending between the interior wall 60 and the exterior wall 62. As shown in FIGS. 6A to 8B, a first pin 90 is coupled to the first pin hole 84 and extending into the first pin slot 80, and a second in 92 is coupled to the second pin hole 86 and extending into the second pin slot 82. The pins 90, 92 regulate linear movement of the collet 22 to the length of each pin slot 80, 82. The pins 90, 92 bottom out in the slots 80, 82 which stops axial movement of the collet 22 and causes it to expand as the head portion 19 of the bone screw 12 continues to push up, as shown in FIG. 6B.

Figure 10A:
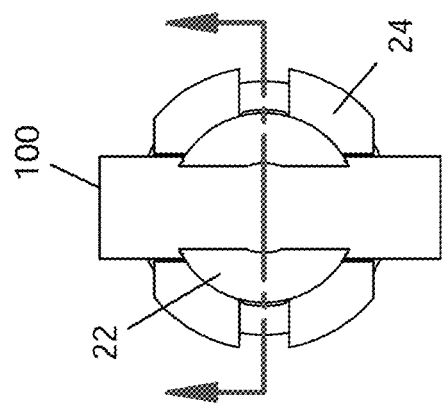
FIG. 10A illustrates a top view of the modular spinal fixation screw with a rod element positioned within the unlocked connector.
Figure 10B:
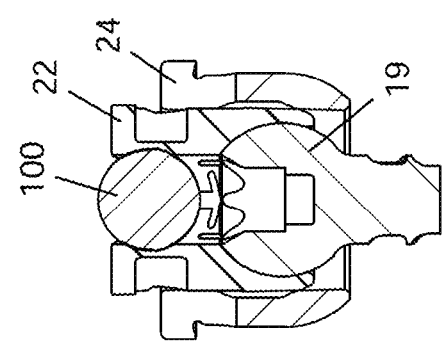
FIG. 10B illustrates a cross-sectional side view taken along line AA of FIG. 10A.
Figure 11A:
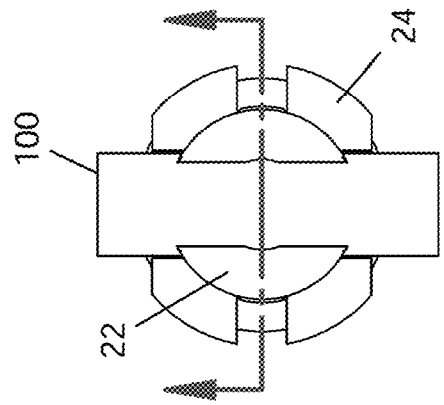
FIG. 11A illustrates a top view of the modular spinal fixation screw with a locked connector and locked rod member.
Figure 11B:
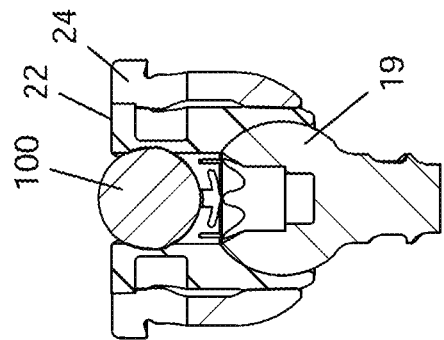
FIG. 11B illustrates a cross-sectional side view taken along line AA of FIG. 11A.

The collet 22 is linearly traversable between a first position and a second position by application of a linear force applied along a longitudinal axis of the clamp 24. Traversal of the collet 22 from the first position to the second position causes the collet 22 to cooperate with the at least one annular bulge 64 to apply concurrent compressive forces to simultaneously immobilize movement between the connector 20 and the rod member 100 and immobilize movement between the connector 20 and the bone screw 12. The loading of the rod member 100 is shown in FIGS. 10A and 10B and the locking of the rod member 100 is shown in FIGS. 11A and 11B. In an alternative embodiment, the collet 22 includes at least one inner annular ridge 66 constructed and arranged to engage the at least one annular bulge 64 in an overlapping manner while the collet 22 is in the second position, whereby engagement of the at least one annual bulge 64 and the at least one annular ridge 66 applies compressive forces to the clamp 24 for immobilizing the clamp 24 to the head portion 19 of the anchored bone screw 12. Further, in another construction, the collet 22 may include one inner annular surface 67 constructed and arranged to engage the at least one annular upper bulge 65 in an overlapping manner while the collet 22 is in the second position, whereby engagement of the at least one annular upper bulge 65 and the at least one annular surface 67 applies compressive forces to said clamp 24 for immobilizing said clamp 24 to said rod member 100.

Figure 6A:
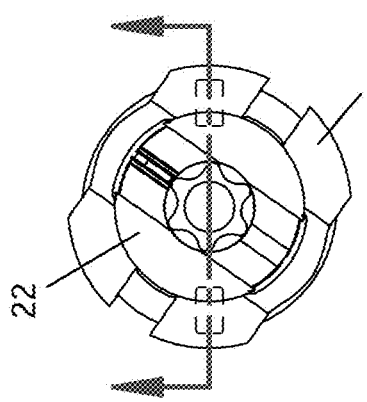
FIG. 6A illustrates a top view of the modular spinal fixation screw with an unlocked connector in a position to be placed upon a bone screw.
Figure 6B:
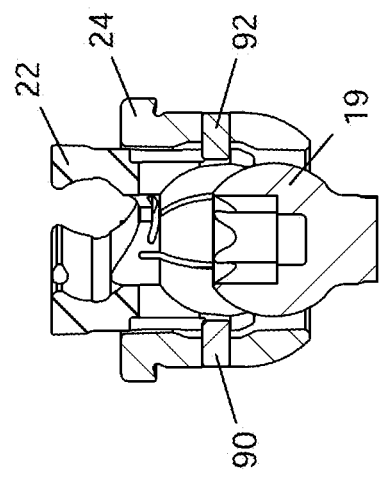
FIG. 6B illustrates a cross-sectional side view taken along line AA of FIG. 6A.
Figure 7B:
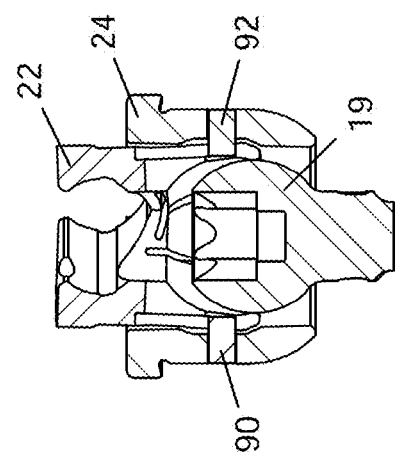
FIG. 7B illustrates a cross-sectional side view taken along line AA of FIG. 7A.
Figure 8B:
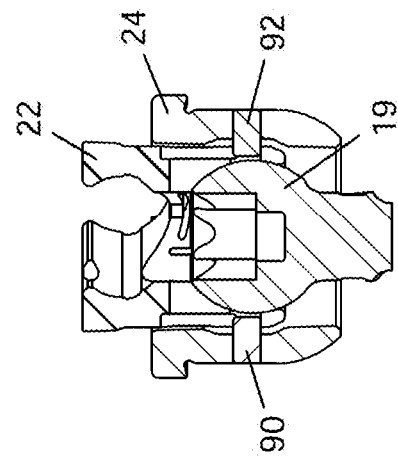
FIG. 8B illustrates a cross-sectional side view taken along line AA of FIG. 8A.
Figure 9A:
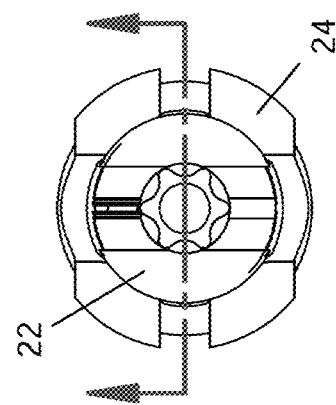
FIG. 9A illustrates a top view of the modular spinal fixation screw with an unlocked connector placed over the bone screw.
Figure 9B:
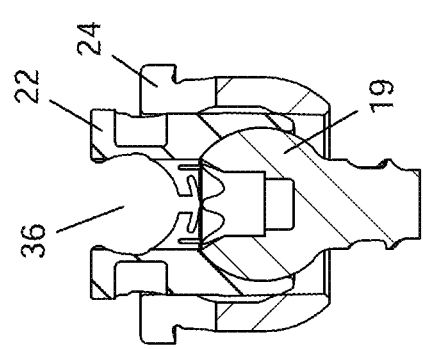
FIG. 9B illustrates a cross-sectional side view taken along line AA of FIG. 9A.

FIG. 6B illustrates the modular spinal fixation screw with the clamp 24 in receipt of the collet 22 in an unlocked position with the connector being placed over the head portion 19 of the bone screw. FIG. 7B illustrates the modular spinal fixation screw with the connector partially placed over the head portion 19 of the bone screw. FIG. 8B illustrates the modular spinal fixation screw with the head portion 19 of the bone screw within the collet 22, the pins 90, 92 keeping the alignment of the collect 22 in response to the clamp 24. FIG. 9B illustrates the modular spinal fixation screw in axial alignment for receipt of a rod member with the connector in an unlocked position. FIG. 10B illustrates the modular spinal fixation screw with rod member 100 placed within the collet 22 with the connector in an unlocked position. FIG. 11B illustrates the modular spinal fixation screw in a locked position coupling the rod member 100 to the head portion 19 of the bone screw.

The term "coupled" is defined as connected, although not necessarily directly, and not necessarily mechanically. The use of the word "a" or "an" when used in conjunction with the term "comprising" in the claims and/or the specification may mean "one," but it is also consistent with the meaning of "one or more" or "at least one." The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a device that "comprises," "has," "includes" or "contains" one or more elements, possesses those one or more elements, but is not limited to possessing only those one or more elements. Likewise, a step of a method or an element of a device that "comprises," "has," "includes" or "contains" one or more features, possesses those one or more features, but is not limited to possessing only those one or more features.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

The invention claimed is:

1. A modular spinal fixation screw comprising:
a bone screw having a first end and a second end with a threaded shank therebetween, said first end for penetrating securement to bone, said second end forming a spherical head portion;
a connector consisting of a collet operatively associated with a clamp, said collet having a lower end spaced apart from an upper end with a cylindrical shaped side wall therebetween, said upper end forming a header which protrudes outwardly from said side wall with a tapered section extending from said side wall to said upper end, a u-shaped receptacle extending beneath said upper end constructed and arranged to receive a rod member, said collet lower end having an inner side wall forming a receptacle surface sized for coupling to said head portion of said bone screw, said receptacle surface having at least one T-shaped living hinge formed therein from a first relief cut extending from said collet lower end to a perpendicular positioned relief cut juxtapositioned to said lower receptacle surface, said collet including a split line extending between said receptacle surface and said lower end; said relief cuts placed between said living hinge and said split line, said collet including first and second vertically disposed pin slots extending along a length of said side wall;
said clamp having an elongated body with an interior wall and an exterior wall, said interior wall including at least one annular bulge constructed and arranged to change the diameter of said collet sidewall when said clamp is drawn over said collet, a rod slot constructed to accept a rod member, said clamp including a first and second pin holes extending between said interior wall and said exterior wall; and
first and second pins, said first pin coupled to said first pin hole and extending into said first pin slot, said second pin coupled to said second pin hole and extending into said second pin slot wherein said pins regulate linear movement of said collet;
wherein said collet is linearly traversable between a first position and a second position by application of a linear force applied along a longitudinal axis of said clamp, whereby traversal of said collet from said first position to said second position causes said collet to cooperate with said at least one annular bulge to apply concurrent compressive forces to simultaneously immobilize movement between said connector and said rod member and immobilize movement between said connector and said bone screw.

2. The modular spinal fixation screw according to claim 1 wherein said collet includes a second pair of relief cuts placed between said split line and said living hinge.

3. The modular spinal fixation screw according to claim 1 including side wall reliefs to facilitate securing said collet to said bone screw head.

4. The modular spinal fixation screw according to claim 1 wherein said collet includes at least one inner annular ridge constructed and arranged to engage said at least one annular bulge in an overlapping manner while said collet is in said second position, whereby engagement of said at least one bulge and said at least one ridge applies compressive forces to said clamp for immobilizing said clamp to said head of the anchored bone screw.

5. The modular spinal fixation screw according to claim 1 wherein said collet includes one inner annular surface constructed and arranged to engage said at least one annular upper bulge in an overlapping manner while said collet is in said second position, whereby engagement of said at least one annular upper bulge and said at least one annular surface applies compressive forces to said clamp for immobilizing said clamp to said rod member.

6. The modular spinal fixation screw according to claim 1 wherein said at least one annular bulge is constructed and arranged to cooperate with said collet to apply compressive forces to said clamp for immobilizing connections between said rod and said anchored bone screw.

7. The modular spinal fixation screw according to claim 1 wherein said bone screw includes at least one helical thread for penetrating and engaging a bone and wherein said head portion is at least partially spherical in shape.

8. A modular spinal fixation screw comprising:
a bone screw having a first end and a second end with a threaded shank therebetween, said first end for penetrating securement to bone, said second end forming a spherical head portion;
a connector consisting of a collet operatively associated with a clamp, said collet having a lower end spaced apart from an upper end with a cylindrical shaped side wall therebetween, said upper end forming a header which protrudes outwardly from said side wall with a tapered section extending from said side wall to said upper end, a u-shaped receptacle extending beneath said upper end constructed and arranged to receive a rod member, said collet lower end having an inner side wall forming a receptacle surface sized for coupling to said head portion of said bone screw, said receptacle surface having at least one T-shaped living hinge formed therein from a first relief cut extending from said collet lower end to a perpendicular positioned relief cut juxtapositioned to said lower receptacle surface, said collet including a split line extending between said receptacle surface and said lower end, said collet includes relief cuts placed between said living hinge and said split line, said collet including first and second vertically disposed pin slots extending along a length of said side wall;
said clamp having an elongated body with an interior wall and an exterior wall, said interior wall including at least one annular bulge constructed and arranged to change the diameter of said collet sidewall when said clamp is drawn over said collet, a rod slot constructed to accept a rod member, said clamp including a first and second pin holes extending between said interior wall and said exterior wall; and
a first pin coupled to said first pin hole and extending into said first pin slot, and a second pin coupled to said second pin hole and extending into said second pin slot, wherein said pins regulate linear movement of said collet to the length of each pin slot;
wherein said collet is linearly traversable between a first position and a second position by application of a linear force applied along a longitudinal axis of said clamp, whereby traversal of said collet from said first position to said second position causes said collet to cooperate with said at least one annular bulge to apply concurrent compressive forces to simultaneously immobilize movement between said connector and said rod member and immobilize movement between said connector and said bone screw.

9. The modular spinal fixation screw according to claim 8 including side wall reliefs to facilitate securing said collet to said bone screw head.

* * * * *